US006261523B1

(12) United States Patent
Schembri

(10) Patent No.: US 6,261,523 B1
(45) Date of Patent: Jul. 17, 2001

(54) ADJUSTABLE VOLUME SEALED CHEMICAL-SOLUTION-CONFINEMENT VESSEL

(75) Inventor: Carol T. Schembri, San Mateo, CA (US)

(73) Assignee: Agilent Technologies Inc., Palo Alto, CA (US)

( * ) Notice: Subject to any disclaimer, the term of this patent is extended or adjusted under 35 U.S.C. 154(b) by 0 days.

(21) Appl. No.: 09/299,976

(22) Filed: Apr. 27, 1999

(51) Int. Cl.[7] ........................................................ B01L 3/00
(52) U.S. Cl. ...................... 422/102; 73/864.62; 220/789; 220/801; 435/258.3; 435/305.1; 435/305.4
(58) Field of Search ...................... 422/102; 435/288.3, 435/305.1, 305.4; 220/780, 789, 796, 801; 73/864.62

(56) References Cited

U.S. PATENT DOCUMENTS

| | | |
|---|---|---|
| 660,435 | 10/1900 | Hilgenberg et al. . |
| 2,767,754 | * 10/1956 | Lederer et al. . |
| 3,494,496 | 2/1970 | Livingstone . |
| 3,976,216 | 8/1976 | Lambert . |
| 4,090,636 | * 5/1978 | Norton . |
| 4,643,033 | 2/1987 | Solazzi ............................... 73/864.91 |
| 4,726,480 | 2/1988 | Hagan . |
| 4,889,691 | 12/1989 | Argentieri ............................. 422/102 |
| 4,893,636 | 1/1990 | Cook et al. . |
| 4,908,319 | * 3/1990 | Smyczek et al. . |
| 4,912,034 | 3/1990 | Kalra et al. . |
| 4,912,037 | * 3/1990 | Lemonnier . |
| 4,916,056 | 4/1990 | Brown, III et al. . |
| 5,064,083 | 11/1991 | Alexander et al. . |
| 5,091,800 | 2/1992 | Offenbacher et al. . |
| 5,145,094 | 9/1992 | Perlmutter . |
| 5,254,314 | 10/1993 | Yu et al. . |
| 5,433,330 | 7/1995 | Yatsko et al. . |
| 5,681,742 | 10/1997 | MersKelly et al. . |

FOREIGN PATENT DOCUMENTS

| | | |
|---|---|---|
| 4016617 | 11/1991 | (DE) . |
| 0 245 994 | 11/1987 | (EP) . |
| 361819 | 5/1906 | (FR) . |
| 2 248 984 | 5/1975 | (FR) . |
| 320112 | 10/1929 | (GB) . |
| 2 106 083 | 4/1983 | (GB) . |
| 98/55232 | 12/1998 | (WO) . |

* cited by examiner

Primary Examiner—Jan Ludlow

(57) ABSTRACT

An adjustable-volume, sealed chemical-solution-confinement vessel for enclosing the inner bottom surface of the chemical-solution-confinement vessel within a sealed chamber. The chemical-solution-confinement vessel comprises a well-shaped base into which a complementarily-shaped lid is inserted. The lid can be inserted to a first position, in order to create a small volume sealed chamber above the inner bottom surface of the chemical-solution-confinement vessel, and can be retracted to a second position in order to create a larger volume sealed chamber above the inner bottom surface of the chemical-solution-confinement vessel. The lid may contain a port or aperture for introducing a fluid or material into the sealed chamber.

8 Claims, 3 Drawing Sheets

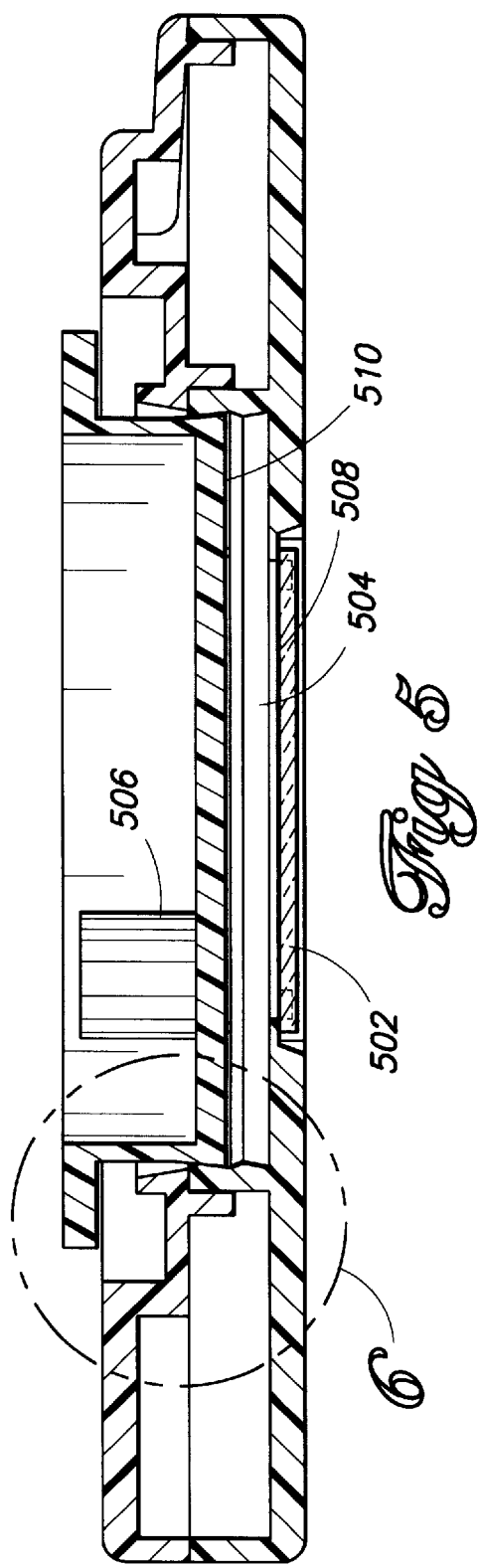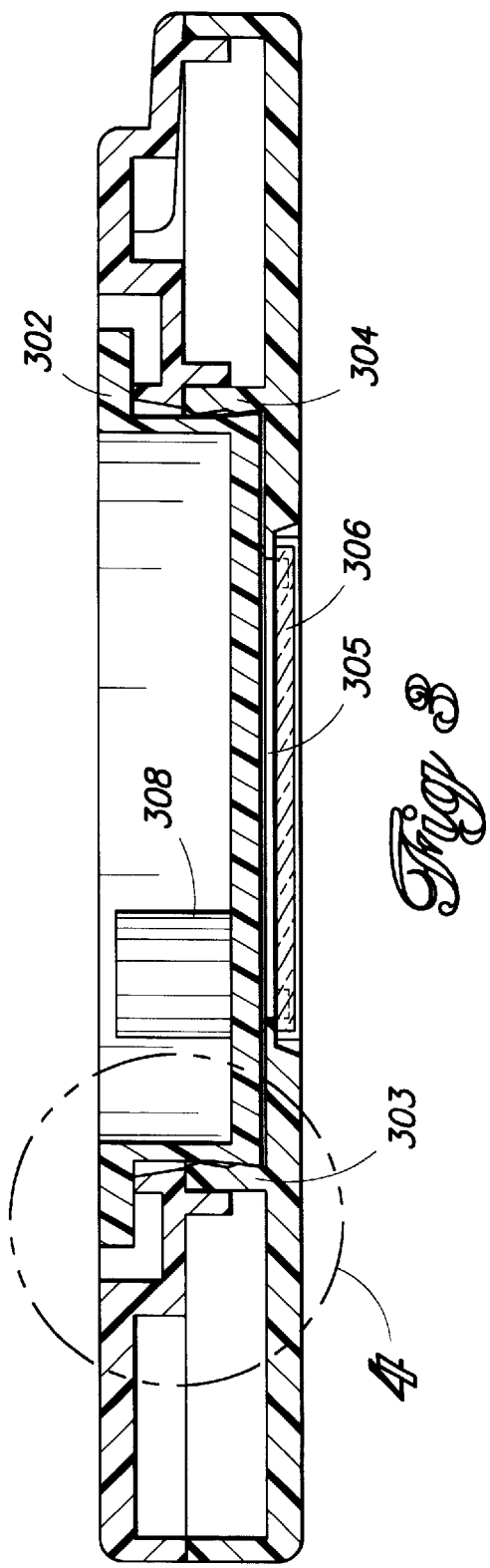

ADJUSTABLE VOLUME SEALED CHEMICAL-SOLUTION-CONFINEMENT VESSEL

TECHNICAL FIELD

The present invention relates to containers that can be closed with lids to produce sealed chambers and, in particular, to a sealed chemical-solution-confinement vessel in which the position of the lid can be moved in order to adjust the volume of the sealed chemical-solution-confinement vessel and to a method for introducing a sample solution into the sealed chemical-solution-confinement vessel and for removing the sample solution from the sealed chemical-solution-confinement vessel.

BACKGROUND OF THE INVENTION

Molecular arrays are widely used and increasingly important tools for rapid hybridization analysis of sample solutions against hundreds or thousands of precisely ordered and positioned features containing different types of molecules within the molecular arrays. Molecular arrays are normally prepared by synthesizing or attaching a large number of molecular species to a chemically prepared substrate such as silicone, glass, or plastic. Each feature, or element, within the molecular array is defined to be a small, regularly-shaped region of the surface of the substrate. The features are arranged in a regular pattern. Each feature within the molecular array may contain a different molecular species, and the molecular species within a given feature may differ from the molecular species within the remaining features of the molecular array. In a hybridization experiment, a sample solution containing radioactively, fluorescently, or chemoluminescently labeled molecules is applied to the surface of the molecular array. Certain of the labeled molecules in the sample solution may specifically bind to, or hybridize with, one or more of the different molecular species that together comprise the molecular array. Following hybridization, the sample solution is removed by washing the surface of the molecular array with a buffer solution, and the molecular array is then analyzed by radiometric or optical methods to determine to which specific features of the molecular array the labeled molecules are bound. Thus, in a single experiment, a solution of labeled molecules can be screened for binding to hundreds or thousands of different molecular species that together comprise the molecular array. Molecular arrays commonly contain oligonucleotides or complementary deoxyribonucleic acid ("cDNA") molecules to which labeled deoxyribonucleic acid ("DNA") and ribonucleic acid ("RNA") molecules bind via sequence-specific hybridization.

Molecular arrays are generally rather large, commonly having surface areas of between 4 and 16 $cm^2$. The volumes of solutions of labeled molecules applied to the surfaces of molecular arrays may be quite small, on the order of between 50 and 100 $\mu L$. Thus, when an applied solution is evenly distributed across the surface of a molecular array, the applied solution may have a thickness of anywhere between thirty and several hundred microns.

There are a number of problems associated with manipulating small volumes of sample solution during the course of a hybridization experiment. First, the sample solution must be evenly distributed across the surface of the molecular array. Second, in many types of hybridization experiments, the sample solution, once distributed across the surface of the molecular array, needs to be enclosed within a sealed container in order to prevent evaporation of the sample solution during the time required for hybridization to occur. Third, once hybridization has completed, any remaining unbound labeled molecules must be rinsed from the surface of the molecular array. Finally, in many hybridization experiments, the surface of the molecular array must remain hydrated by a buffer solution until binding of labeled molecules to the surface of the molecular array is detected by radiometric or optical methods. It is desirable for the entire process to be automated to as great an extent as possible in order to increase the accuracy and throughput of hyridization screening.

Currently, experimenters may use a manual approach to solve these problems. A silicone gel or other such non-reactive, water impermeable substance may be placed along the edges of the molecular array, sample solution placed onto the center of the molecular array, and a glass cover slip placed on top of the sample solution in order to press the sample solution down towards the surface of the molecular array and distribute it across the surface of the molecular array. The glass cover slip makes contact with the silicone gel at the edges of the molecular array to form a seal enclosing the sample solution between the surface of the molecular array, the glass cover slip, and the silicone gel. However, this method is tedious and time consuming, especially in view of the fact that the glass cover slip must be removed in order to rinse the surface of the molecular array prior to radiometric or optical analysis. Another approach is to embed the molecular array within the surface of a plastic housing with a continuous side wall that forms an open well, or container, with the molecular array at the bottom of the well. After the sample solution is applied to the molecular array, the plastic housing is covered with a lid to form a seal enclosing a relatively small volume above the surface of the molecular array, and the housing and molecular array is then spun in a centrifuge to apply centrifugal force to the sample solution in order to spread the sample solution evenly across the surface of the molecular array. Once distributed across the surface of the molecular array, capillary action holds the sample solution to the surface of the molecular array during the time required for hybridization. Following hybridization, the lid is removed from the plastic housing in order to rinse away any remaining unbound, unlabeled molecules, and a replacement buffer solution is added to the container, followed by replacement of the lid.

While more amenable to automation, the second technique may limit the accuracy and reliability of optical analysis of fluorescently labeled, bound sample molecules. In common optical analysis techniques, a pinpoint laser beam scans the surface of the molecular array in order to excite fluorophores bound to sample molecules hybridized with molecular array molecules. The laser beam passes through the molecular array substrate in order to reach the bound molecules, continues into the buffer solution distributed across the surface of the molecular array, and is finally absorbed by the lid enclosing the well or container in a seal. Because the sample volumes are small, the lid is positioned quite close to the inner surface of the molecular array, on an order of 3 to 5 thousandths of an inch. The laser beam, under these conditions, may effectively excite naturally occurring fluorophores within the lid as well as fluorophores bound to sample molecules. When fluorescence is subsequently measured by optically focused measuring devices, fluorescence from the naturally occurring fluorophores within the lid may add significant background to the fluorescence emanating from the fluorophores bound to sample molecules, decreasing the signal-to-noise ratio of the measured fluorescent emissions from the sample molecules. To decrease the background fluorescence emanating from the lid, the lid may be manufactured from materials chosen to have very low concentrations of natural fluorophores. Glass is one such substance, but the manufacture and manipulation of glass lids may be expensive and prone to mechanical damage. Another approach is to add light-absorbing filler, such as carbon black, to plastics in order to absorb fluorescent emissions internally within the lid. However, this approach has failed to sufficiently reduce the contribution to background fluorescence from naturally occurring fluorophores in the lid. Thus, manufacturers of molecular arrays and experimenters using molecular arrays for hybridization screening have recognized the need for a straightforward technique and apparatus, amenable to automation, for manipulating small volumes of sample solutions tightly sealed within close proximity to the surfaces of molecular arrays and for optically measuring the fluorescence of fluorescently labeled sample molecules bound to the surface of molecular arrays.

SUMMARY OF THE INVENTION

In one embodiment of the present invention, the substrate of a molecular array is embedded within a plastic base with a continuous inner side wall to form a well above the surface of the molecular array. A lid with two cylindrical aperture housings orthogonal to the plane of the lid is fitted to a first position within the plastic base, directly above and parallel with the surface of the molecular array to create a small, sealed chamber above the surface of the molecular array. A small volume of sample solution can be introduced into this enclosed chamber via a first needle passing through a septum within a first cylindrical aperture housing. A second needle is inserted through the septum sealing a second cylindrical aperture housing to vent the enclosed chamber, allowing the sample solution to spread across the surface of the molecular array via capillary action. Suction may be applied to the second needle to draw the sample solution across the surface of the molecular array, and pressure can be applied to the sample solution via a syringe attached to the first needle. In an alternate embodiment, a single cylindrical aperture housing is incorporated into the lid. Sample solution is introduced into the enclosed chamber via a needle inserted through a septum covering the aperture, and the adjustable-volume, sealed chemical-solution-confinement vessel is then spun in a centrifuge to distribute the sample solution across the surface of the molecular array by centrifugal force. After binding of labeled molecules within the sample solution to molecules bound to the surface of the molecular array, the lid can be retracted away from the surface of the molecular array to a second position, resulting in a sealed chamber of a much larger volume above the surface of the molecular array. The larger enclosed chamber facilitates removal of the sample solution from the surface of the molecular array by rinsing the surface of the molecular array with a buffer solution. Moreover, in the second position, naturally occurring fluorophores within the lid are spatially removed from the surface of the molecular array, where fluorescence emitted by these naturally occurring fluorophores contributes only a low, diffuse, unfocused background fluorescence during optical measuring of the fluorescence emitted from fluorophores bound to sample molecules.

BRIEF DESCRIPTION OF THE DRAWINGS

FIG. 3 shows a vertical cross-section of the adjustable-volume, sealed chemical-solution-confinement vessel.

FIG. 5 is a cross-section view of the adjustable-volume, sealed chemical-solution-confinement vessel with the lid retracted to a second, stable position.

DETAILED DESCRIPTION OF THE INVENTION

Figure 1:
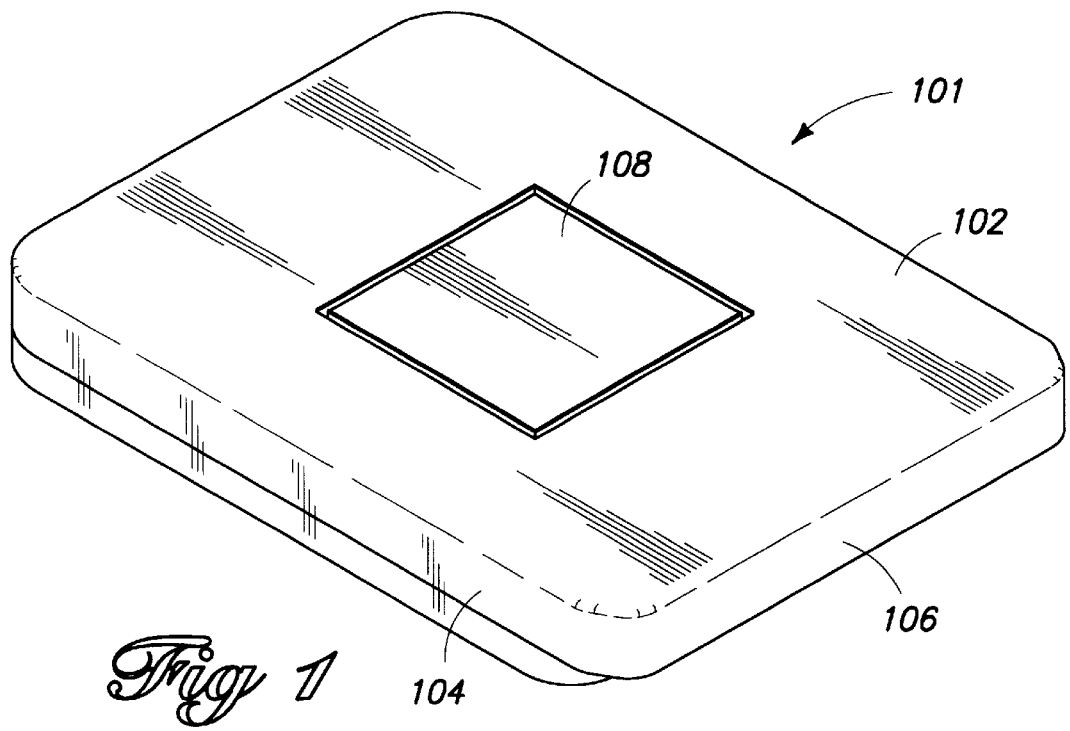
FIG. 1 shows a view of the adjustable-volume chemical-solution confinement vessel looking down on the bottom exterior surface of the base.

One embodiment of the present invention relates to an adjustable-volume, sealed chemical-solution-confinement vessel for confining small solution samples in a sealed enclosure on the surface of a molecular array. In this embodiment, the adjustable-volume, sealed chemical-solution-confinement vessel comprises a base that includes the molecular array and a lid that forms a seal in two positions in order to enclose a very small volume, in the first position, and a larger volume, in the second position, above the surface of the molecular array. The molecular array can be prepared according to standard molecular array preparation techniques and then affixed to a bottom, external side of a collar that extends horizontally from the base and that frames an aperture within the base slightly smaller than the molecular array substrate, with the molecular array confined within a region of the surface of the molecular array substrate underlying the aperture. The molecular array is affixed to the base to form a seal. The various molecular species bound to features, or elements, of the molecular array are located on the inner surface of the molecular array at the bottom of a well formed by the molecular array substrate, the flat, bottom portion of the base, and an inner continuous side wall of the base that extends perpendicularly from the plane of the bottom of the base. A well-shaped lid having vertical sides slightly flaring toward the flat bottom of the lid, with a shape complementary to the shape of the well formed by the base and the inner, continuous side wall of the base, is snugly inserted into the well of the base so that the lower surface of the lid is parallel to, and directly above, the inner surface of the molecular array substrate. A seal is accomplished by positioning the flared bottom edge of the lid within a circumferential depression around the inner surface of the well of the base with the edge of the lid pressing against a circumferential member on the inner surface of the well. In this embodiment, there are two such circumferential depressions. The first circumferential depression is located close to the bottom inner surface of the well of the base, and the second circumferential depression is located further away from the inner surface of the well of the base. When the lid is snugly fitted to the first circumferential depression, close to the inner surface of the base, the inner surface of the molecular array substrate, the inner surface of the bottom and inner, continuous, side wall of the base, and the bottom surface of the lid together form a sealed chamber above the plane of the inner surface of the molecular array substrate. When the flared bottom edge of the lid is positioned in the second circumferential depression, a larger sealed chamber above the plane of the inner surface of the molecular array substrate is formed.

During the initial portion of a hybridization experiment, the lid is snugly fit into the first circumferential depression to create a small volume chamber. A sample solution containing labeled molecules is introduced into this small volume chamber from a needle via a first cylindrical aperture housing rising vertically from the top surface of the bottom portion of the lid and sealed with a flexible membrane, or septum, while the small volume chamber is vented through a second needle inserted through a septum sealing a second cylindrical aperture housing. The sample solution spreads across the surface of the molecular array via capillary action, and may be assisted in spreading via pressure exerted from the syringe. In an alternate embodiment, a single cylindrical aperture housing is incorporated into the lid, through which sample solution is introduced into the small volume chamber via a needle. However, in this alternate embodiment, after the sample solution has been introduced into the chamber, the entire adjustable-volume, sealed chemical-solution-confinement vessel is spun in a centrifuge in order to distribute the sample solution across the inner surface of the molecular array substrate.

Once the sample solution has been distributed across the surface of the molecular array, the sample solution is held in place by capillary action.

Hybridization between molecules in the sample solution and molecules affixed to the inner surface of the molecular array substrate is then allowed to proceed. Following hybridization, the lid is retracted from the first circumferential depression to the second circumferential depression to create a larger volume chamber. Buffer solution can be introduced into the larger volume chamber to rinse the sample solution from the surface of the molecular array substrate via a syringe and needle, and the diluted sample solution can be removed from the larger volume chamber via the syringe and needle. In the preferred embodiment, buffer solution can be introduced into the chamber through one aperture housing while solution is extracted via a syringe from the other aperture housing. In the single-aperture-housing embodiment, buffer solution is introduced into the larger volume chamber through the single aperture housing, and removed by a second centrifugation step via a side port in the base that is exposed when the lid retracted to the second circumferential depression. Following rinsing, a buffer solution may be left in the larger-volume chamber in order to maintain the inner surface of the molecular array in a hydrated state. The larger volume chamber created by retraction of the lid to the second position greatly facilitates sample solution removal and substrate rinsing.

When sample molecules labeled with fluorophores are used, binding of sample molecules to the inner surface of the molecular array substrate is detected by scanning the molecular array substrate with a tightly focused laser beam to excite the fluorophores and then analyzing fluorescent emissions from the fluorophores via an optical measuring device. The optical measuring device is focused to the inner surface of the molecular array substrate. Because the bottom surface of the lid has been retracted away from the molecular array substrate, the fluorescence of naturally occurring fluorophores within the lid material is both attenuated by distance and removed from the plane of focus of the optical measuring device. Thus, fluorescent emission from any naturally occurring fluorophores in the lid contribute to a low, diffuse, and unfocused background fluorescence that does not significantly degrade the signal-to-noise ratio of the optically measured fluorescence from fluorophores bound to sample molecules hybridized with molecules bound to the surface of the molecular array.

FIG. 1 shows a view of the adjustable-volume, sealed chemical-solution-confinement vessel looking down on the bottom exterior surface of the base. The base comprises a single, molded plastic, well-shaped container 101 comprising a flat bottom 102 with a continuous outer side wall 104 and 106. The molecular array substrate 108 is inset into a square aperture in the bottom 102 of the base. Fluorescent emissions from fluorophores bound to hybridized molecules are optically measured from the bottom exterior surface of the molecular array substrate, shown in FIG. 1.

Figure 2:
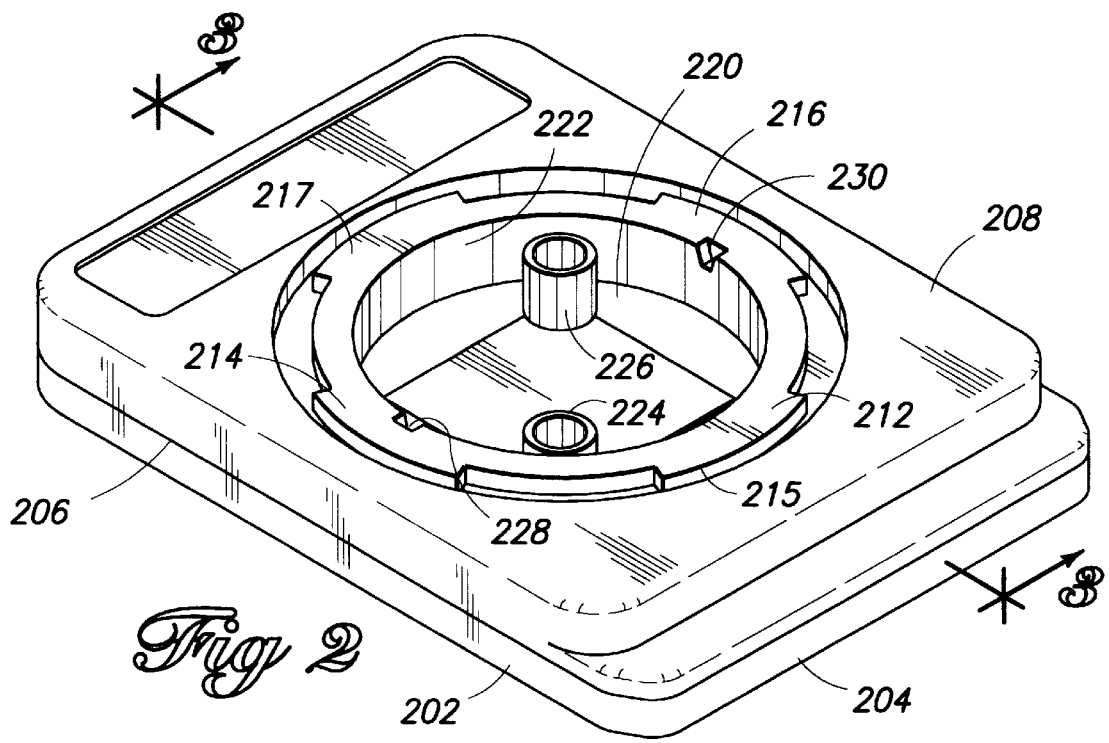
FIG. 2 is a view of the adjustable-volume, sealed chemical-solution-confinement vessel from the opposite side of the adjustable-volume, sealed chemical-solution-confinement vessel as that shown in FIG. 1.

FIG. 2 is a view of the adjustable-volume, sealed chemical-solution-confinement vessel from the opposite side of the adjustable-volume, sealed chemical-solution-confinement vessel as that shown in FIG. 1. The continuous outer side wall of the base 202 and 204 extends upward to a rim 206 that is a planar cross-section of the continuous side wall 202 and 204 parallel with the bottom of the base (bottom not shown in FIG. 2, 102 in FIG. 1). A molded cover plate 208 is permanently affixed to the rim 206. The cover plate includes a large circular aperture through which a lid 210 is inserted and fitted to the continuous side wall of the base (not shown in FIG. 2). The lid comprises, in one molded piece, an annular collar 212 with four tabs 214–217, a disk-shaped bottom 220, a continuous annular side wall 222 that connects the annular collar 212 to the disk-shaped bottom 220, and two vertical aperture housings 224 and 226 rising orthogonally to the plane of the bottom of the lid 220 above circular apertures in the bottom of the lid (not shown). The circular apertures are covered by flexible membranes, or septa (not shown in FIG. 2). There are two notches 228 and 230 in the inner rim of the annular collar 212 and annular side wall 222 of the lid. The tabs 214–217 and notches 228 and 230 provide surfaces to which a lid insertion and extraction tool mates. The lid insertion and extraction tool (not shown in Figures) provides a sloping, helical lever that raises and lowers the lid 210 via rotation of the insertion and extraction tool about a longitudinal axis of the insertion and extraction tool.

Figure 4:
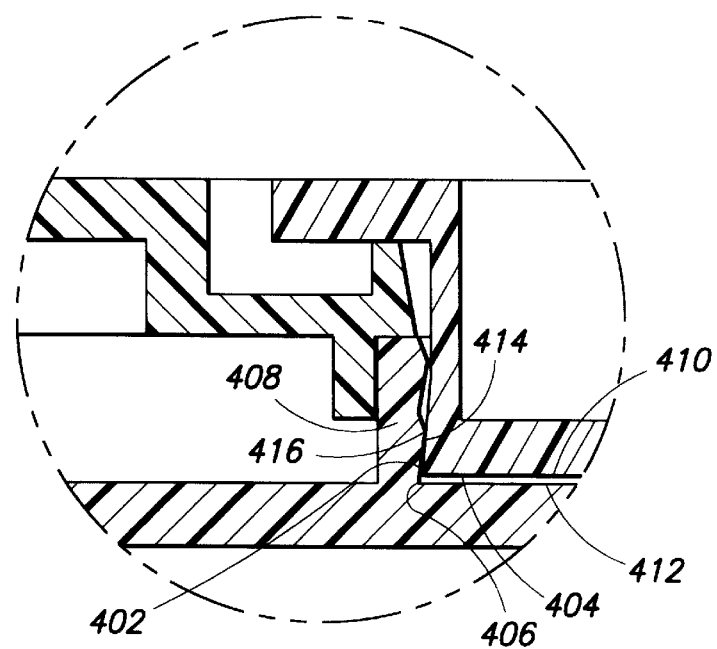
FIG. 4 shows a larger scale view of the interface between the lid and the base.

FIG. 3 shows a vertical cross-section of the adjustable-volume, sealed chemical-solution-confinement vessel, and FIG. 4 shows a larger-scale view of the interface between the lid and base. The lid 302 is fully inserted into a well formed by the interior surface of the base 412 and an inner continuous side wall of the base 303 and 304 in order to create a small chamber 305 above the surface of the molecular array substrate 306. The slightly flared, external surface of the annular side wall 402 and bottom 404 of the lid snugly fit within a circumferential depression 406 on the interior surface of the inner side wall 408 of the base, with the bottom surface of the lid 410 flush with the interior surface of the base 412. A seal is effected by pressing of the exterior continuous annular side wall of the lid 414 against a continuous, circumferential, raised member 416 on the interior side wall of the well of the base. A sample solution may be introduced into the chamber 305 from a needle (not shown) by inserting the needle into the aperture housing 308, through a septum covering the aperture at the base of the aperture housing 308 (septum not shown). When the needle is removed, the hole in the septum closes on itself to form a seal. A needle inserted through the second aperture housing (not shown in FIG. 3) vents the chamber 305 to allow the sample solution to spread across the surface of the molecular array via capillary action. Alternatively, suction can be applied to the second needle to draw the sample solution across the surface of the molecular array.

The adjustable-volume, sealed chemical-solution-confinement vessel, including the lid positioned as shown in FIG. 3, is spun in a centrifuge to distribute the sample fluid across the inner surface of the molecular array substrate 306.

The adjustable-volume, sealed chemical-solution-confinement vessel can then minutes or hours so that hybridization between labeled molecules in the sample solution and molecules bound to the inner surface of the molecular array substrate can occur.

Figure 6:
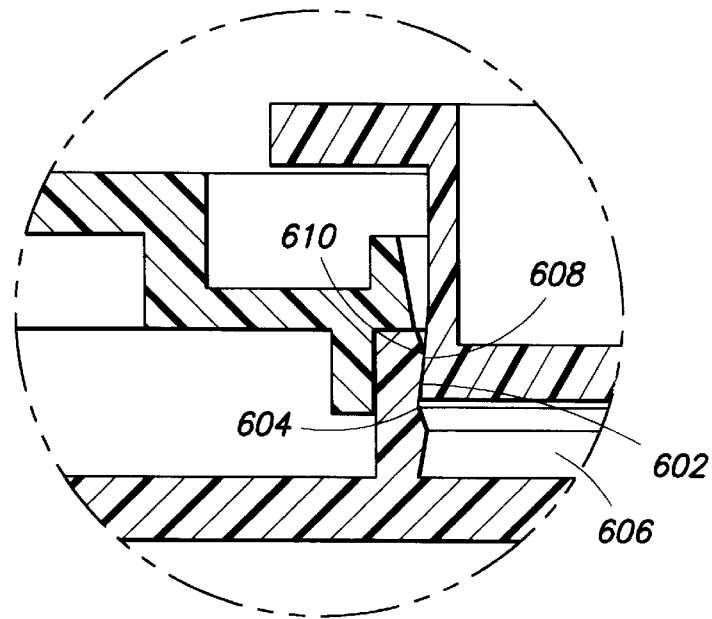
FIG. 6 shows a larger scale view of the interface between the lid and the base in a second, stable position.

FIG. 5 is a cross-section view of the adjustable-volume, sealed chemical-solution-confmement vessel with the lid retracted to a second, stable position, and FIG. 6 shows a larger scale view of the interface between the lid and base in the second, stable position. In FIG. 6, the flared outer rim of the lid 602 is resting in a circumferential depression in the inner surface of the inner continuous side wall of the base 604 to create a larger volume chamber 606 above the inner surface of the molecular array substrate (502 in FIG. 5). A seal is effected by pressure of the outer lower surface of the continuous annular side wall of the lid 608 against a raised, rounded annular member 610 on the inner surface of the inner continuous side wall of the base. Following hybridization, a buffer solution of significantly greater volume than the sample solution can be introduced via a syringe and needle into the larger-volume chamber 504 and removed via a syringe and needle inserted into the vertical housing 506. Following rinsing, a buffer solution can be maintained in the larger volume chamber 504 in order to maintain the inner surface of the molecular array in a hydrated state. With the lid retracted to the second stable position, shown in FIG. 5, fluorescent emissions from fluorophores bound to the inner surface of the molecular array substrate 508 can be optically measured without significant interference from fluorescent emissions from naturally occurring fluorophores within the bottom of the lid 510. Thus, the larger volume chamber 504 facilitates both rinsing of the sample solution from the surface of the molecular array as well as optical measurement of fluorescent emissions from fluorophores bound to the inner surface of the molecular array substrate.

Although the present invention has been described in terms of a particular embodiment, it is not intended that the invention be limited to this embodiment. Modifications within the spirit of the invention will be apparent to those skilled in the art. For example, the base and lid may be molded from any of a variety of different plastic materials. In a preferred embodiment, the base and lid are injection molded using a flexible plastic such as polypropylene. The base and lid may be manufactured in a variety of different shapes and sizes to accommodate different shapes and sizes of molecular arrays. In some cases, molecular arrays are square or rectangular, and in other cases, they are circular disks. In one embodiment, only a single vertical aperture housing is incorporated into the lid. Solutions are introduced into the chamber between the lid and the surface of the molecular array through the single vertical aperture housing and extracted via a side port in the base. In a preferred embodiment, two vertical aperture housings are incorporated into the lid so that a rinse solution may be introduced into the chamber via a first vertical aperture housing concurrently with extraction of the rinse solution via a second vertical aperture housing. In alternative embodiments, additional vertical aperture housings may be incorporated into the lid. In alternative embodiments, additional circumferential depressions and rounded members may be incorporated into the inner surface of the continuous side wall of the base in order to provide additional stable placements for the lid so that a larger number of chamber volumes can be produced by moving the lid from one position to another. The molecular array substrate may be affixed to the base using a variety of different temporary, semi-permanent, and permanent sealants. In another alternative embodiment, 0-rings or other such annular members may be incorporated into the continuous side wall of the base in order to implement the stable lid positions. In the described embodiment, the molecular array substrate may be affixed to a bottom surface of a collar so that the bottom surface of the molecular array substrate is flush with the bottom, external side of the base. The molecular array substrate may, alternatively, be mounted to the top surface of a collar that is flush with the bottom, external side of the base. In other words, the molecular array substrate may be mounted into a framed aperture from one side of the base, in one embodiment, and from the opposite side of the base, in an alternative embodiment. In alternative embodiments, the molecular array may be prepared on a bottom transparent surface of a single-piece base, obviating the need for a separate molecular array substrate. In the described embodiment, the stable lid positions are formed by areas between members extending inward from the inner surface of the continuous side wall of the base. In an alternative embodiment, depressions can be introduced into the inner surface of the continuous side wall of the base in order to provide stable resting positions for the lid. In alternative embodiments, ports or apertures may be incorporated into the base, rather than into the lid, as shown in the embodiment discussed, and the shapes and sizes of aperture housings may be varied. In those cases where continuous hydration of the molecular array surface is not required, septa are not required to cover the apertures or ports.

The foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description; they are not intended to be exhaustive or to limit the invention to the precise forms disclosed, obviously many modifications and variations are possible in view of the above teachings. The embodiments were chosen and described in order to best explain the principles of the invention and its practical applications and to thereby enable others skilled in the art to best utilize the invention and various embodiments with various modifications as are suited to the particular use contemplated. It is intended that the scope of the invention be defined by the following claims and their equivalents:

What is claimed is:

1. An adjustable-volume, sealed chemical-solution-confinement vessel comprising:

a base with a continuous side wall, the base and continuous side wall together forming a well shaped, open container, the continuous side wall having an external and an internal side, the base having an internal and an external side;

a plurality of raised, circumferential members on the internal side of the continuous side wall, the circumferential members coplanar with planes parallel to the base; and a lid complementarily shaped to fit within the continuous side wall, the lid having a flared outer lower edge that snugly fits in circumferential depressions adjacent the circumferential members, pressure of the lower edge of the lid against one of the circumferential members forming a seal, the lid movable, in a direction approximately perpendicular to the plane of the base, so that sealed chambers of increasing volumes are formed when the flared outer lower edge of the lid fits in each of the circumferential depressions at increasing distances from the base.

2. The adjustable-volume, sealed chemical-solution-confinement vessel of claim 1 wherein two circumferential depressions adjacent two raised, circumferential members on the internal side of the continuous side wall form two stable positions into which the flared outer lower edge of the lid snugly fit.

3. The adjustable-volume, sealed chemical-solution-confinement vessel of claim 1 wherein a transparent molecular array substrate is embedded into the base, the embedded molecular array substrate having an interior side within and at the bottom of the well-shaped container and an exterior side approximately coplanar with the external surface of the base, the molecular array substrate having molecules bound to the interior side of the molecular array substrate, the molecular array molecules, and any molecules bound to them, accessible from the external side of the molecular array substrate to light beams passing through the molecular array substrate and accessible for analysis of electromagnetic emissions by optical and radiometric instruments.

4. The adjustable-volume, sealed chemical-solution-confinement vessel of claim 1 wherein the base and lid are formed from a flexible plastic material.

5. The adjustable-volume, sealed chemical-solution-confinement vessel of claim 1 wherein the lid includes a port through which materials can be introduced into the sealed chamber.

6. The adjustable-volume, sealed chemical-solution-confinement vessel of claim 5 wherein the port comprises an aperture covered by a flexible, self-sealing membrane.

7. The adjustable-volume, sealed chemical-solution-confinement vessel of claim 5 wherein the port comprises an aperture, an aperture housing, and a flexible, self-sealing membrane sealing the aperture.

8. The adjustable-volume, sealed chemical-solution-confinement vessel of claim 7 wherein a plurality of ports are incorporated into the lid.

* * * * *